(12) United States Patent
Clark et al.

(10) Patent No.: US 11,419,560 B2
(45) Date of Patent: Aug. 23, 2022

(54) METHOD AND APPARATUS FOR MONITORING STATE OF INFLAMMATORY BOWEL DISEASE

(71) Applicant: Boston Scientific Scimed, Inc., Maple Grove, MN (US)

(72) Inventors: Bryan Allen Clark, Forest Lake, MN (US); Elizabeth Mary Annoni, White Bear Lake, MN (US); Sandra Nagale, Bolton, MA (US); Jeffrey E. Stahmann, Ramsey, MN (US); Kyle Harish Srivastava, Saint Paul, MN (US); Mark W. Boden, Harrisville, RI (US); Martin Phelan, Sussex, NJ (US); George Wilfred Duval, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 223 days.

(21) Appl. No.: 16/188,669

(22) Filed: Nov. 13, 2018

(65) Prior Publication Data

US 2019/0150851 A1 May 23, 2019

Related U.S. Application Data

(60) Provisional application No. 62/590,307, filed on Nov. 23, 2017.

(51) Int. Cl.
*A61B 5/00* (2006.01)
*A61B 5/024* (2006.01)
(Continued)

(52) U.S. Cl.
CPC ............ *A61B 5/7275* (2013.01); *A61B 5/024* (2013.01); *A61B 5/02405* (2013.01);
(Continued)

(58) Field of Classification Search
CPC ... A61B 5/7275; A61B 5/4222; A61B 5/1118; A61B 5/024; A61B 5/4216; A61B 5/42;
(Continued)

(56) References Cited

U.S. PATENT DOCUMENTS 7,833,164 B2   11/2010   Scheiner et al.
8,403,865 B2   3/2013    Halperin et al.
(Continued)

FOREIGN PATENT DOCUMENTS

| CN | 111386067 A | 7/2020 |
| WO | WO-2010062663 A1 | 6/2010 |
| WO | WO-2019103870 A1 | 5/2019 |

OTHER PUBLICATIONS

Straub et al. "Association of autonomic nervous hyperreflexia and systemic inflammation in patients with Crohn's disease and ulcerative colitis". Journal of Neuroimmunology, vol. 80, Issues 1-2, Dec. 1997, pp. 149-157.*

(Continued)

*Primary Examiner* — Eugene T Wu
(74) *Attorney, Agent, or Firm* — Schwegman Lundberg & Woessner, P.A.

(57) ABSTRACT

An example of a system for monitoring and treating a medical condition of a patient may include signal inputs to receive patient condition signals indicative of a state of inflammatory bowel disease (IBD), a signal processing circuit configured to process the patient condition signals and generate patient condition parameters indicative of the state of IBD using the processed patient condition signals, and a medical condition analyzer configured to analyze the patient condition parameters and determine the medical condition including the state of IBD using an outcome of the analysis. The patient condition parameters may include one or more physiological marker parameters each representa- (Continued)

tive of a physiological marker of IBD and one or more quality of life parameters each being measure of quality of life of the patient.

20 Claims, 10 Drawing Sheets

(51) Int. Cl.
    *C07K 16/24*     (2006.01)
    *A61B 5/11*     (2006.01)
    *A61K 39/00*     (2006.01)
    *A61B 5/08*     (2006.01)
    *A61B 5/113*     (2006.01)
    *A61B 5/0205*     (2006.01)
    *G16H 50/30*     (2018.01)
    *A61B 5/021*     (2006.01)
    *A61B 5/0245*     (2006.01)

(52) U.S. Cl.
    CPC .............. *A61B 5/1118* (2013.01); *A61B 5/42* (2013.01); *A61B 5/4216* (2013.01); *A61B 5/4222* (2013.01); *A61B 5/4238* (2013.01); *A61B 5/4255* (2013.01); *A61B 5/4839* (2013.01); *A61B 5/7278* (2013.01); *A61B 5/746* (2013.01); *C07K 16/244* (2013.01); *A61B 5/021* (2013.01); *A61B 5/0205* (2013.01); *A61B 5/0245* (2013.01); *A61B 5/08* (2013.01); *A61B 5/113* (2013.01); *A61B 5/4836* (2013.01); *A61B 5/7264* (2013.01); *A61B 5/7282* (2013.01); *A61B 2560/0242* (2013.01); *A61K 2039/505* (2013.01); *G01N 2800/065* (2013.01); *G01N 2800/52* (2013.01); *G01N 2800/60* (2013.01); *G16H 50/30* (2018.01)

(58) Field of Classification Search
    CPC ... A61B 5/7278; A61B 5/02405; A61B 5/746; A61B 5/4839; A61B 5/4238; A61B 5/4255; A61B 5/021; A61B 2560/0242; A61B 5/0245; A61B 5/4836; A61B 5/08; A61B 5/7264; A61B 5/113; A61B 5/0205; A61B 5/7282; G01N 2800/065; G01N 2800/52; G01N 2800/60; A61K 2039/505; G16H 50/30; C07K 16/244
    See application file for complete search history.

(56) References Cited

U.S. PATENT DOCUMENTS

| | | | |
|---|---|---|---|
| 2006/0015263 A1* | 1/2006 | Stupp ...................... | G16H 50/30 702/19 |
| 2009/0258848 A1 | 10/2009 | Chakravarti | |
| 2011/0055141 A1* | 3/2011 | Jamil ...................... | G16H 50/70 706/54 |
| 2011/0212104 A1* | 9/2011 | Beaumont .......... | G01N 33/6893 424/158.1 |
| 2013/0046150 A1* | 2/2013 | Devanaboyina ..... | A61B 5/0024 600/301 |
| 2016/0030752 A1 | 2/2016 | Mahajan et al. | |
| 2017/0079598 A1 | 3/2017 | Stolen et al. | |
| 2017/0196457 A1 | 7/2017 | Thakur et al. | |
| 2017/0196458 A1 | 7/2017 | Ternes et al. | |
| 2017/0199970 A1 | 7/2017 | Stahmann et al. | |
| 2018/0049653 A1* | 2/2018 | Husheer ............... | A61B 5/6823 |
| 2018/0203009 A1* | 7/2018 | Vittorino De Almeida ................. | G16B 20/00 |

OTHER PUBLICATIONS

"Early signs of a Flare", Patient Forum—Citation Downloaded Nov. 8, 2018 11:12 AM (GMT-7), 5 pgs.
"Initial flare symptoms", Patient Forum—Citation Downloaded Nov. 8, 2018 11:12 AM (GMT-7), 7 pgs.
"Pre-flare", Patient Forum—Citation Downloaded Nov. 8, 2018 11:12 AM (GMT-7), 3 pgs.
"What are your flare warning signs?", Patient Forum—Citation Downloaded Nov. 8, 2018 11:12 AM (GMT, 10 pgs.
Al-Shboul, Othman A., "The Importance of Interstitial Cells of Cajal in the Gastrointestinal Tract", The Saudi Journal of Gastroenterology, vol. 19, No. 1, Safar 1434, Jan. 2013, 13 pgs.
Archanioti, Paraskevi, el al., "Micro-RNAs as regulators and possible diagnostic bio-markers in inflammatory bowel disease", Journal of Crohn's and Colitis (2011) 5, 520-524.
Barkas, Fotis, et al., "Electrolyte and acid-base disorders in inflammatory bowel disease", Annals of Gastroenterology (2013) 26, 23-28.
Bernstein, Charles N., et al., "A Prospective Population-Based Study of Triggers of Symptomatic Flares in IBD", Am J Gastroenterol 2010; 105:1994-2002.
Bruno, Maria E.C., "Correlation of Biomarker Expression in Colonic Mucosa with Disease Phenotype in Crohn's Disease and Ulcerative Colitis", Dig Dis Sci. Oct. 2015; 60(10), 17 pgs.
Cooper, Timothy M., et al., "Heart Rate Variability Predicts Levels of Inflammatory Markers: Evidence for the Vagal Anti-Inflammatory Pathway", Brain Behav Immun. Oct. 2015; 49, 16 pgs.
Cracowski, Jean-Luc, et al., "Increased Urinary F2-Isoprostanes in Patients With Crohn's Disease", The American Journal of Gastroenterology, vol. 97, No. 1, 2002, 99-103.
Cury, Didia Bismara, et al., "Serum calprotectin levels correlate with biochemical and histological markers of disease activity in TNBS colitis", Cell Immunol. Mar. 2013; 282(1), 11 pgs.
D'Incà, Renata, et al., "Measuring disease activity in Crohn's disease: what is currently available to the clinician", Clinical and Experimental Gastroenterology 2014:7 151-161.
Deboer, Mark D., et al., "Use of Ghrelin as a Treatment for Inflammatory Bowel Disease: Mechanistic Considerations", International Journal of Peptides, vol. 2011, Article ID 189242, 8 pgs.
Derici, Ulver, et al., "Does the Urinary Excretion of a1-Microglobulin and Albumin Predict Clinical Disease Activity in Ulcerative Colitis?", Adv Ther. 2008; 25(12):1342-1352.
Engel, Tal, et al., "Autonomic Dysfunction Correlates with Clinical and Inflammatory Activity in Patients with Crohn's Disease", Inflamm Bowel Dis vol. 21, No. 10, Oct. 2015, 2320-2326.
Fengming, Yi, et al., "Biomarkers of Inflammatory Bowel Disease", Disease Markers, vol. 2014, Article ID 710915, 11 pgs.
Gunterberg, V., et al., "Autonomic nervous system function predicts the inflammatory response over three years in newly diagnosed ulcerative colitis patients", Neurogastroenterol Motil (2016) 28, 1655-1662.
Haarala, Atte, et al., "Heart rate variability is independently associated with C-reactive protein but not with Serum amyloid A. The Cardiovascular Risk in Young Finns Study", European Journal of Clinical Investigation vol. 41, 2011, 951-957.
Hazratjee, Nyla, et al., "Hospital Readmissions in Patients With Inflammatory Bowel Disease", Am J Gastroenterol 2013;108:1024-1032.
Ilangovan, R., et al., "CT enterography: review of technique and practical tips", The British Journal of Radiology, 85 (2012), 876-886.
Ishii, Genichi, et al., "Clinical evaluation of urolithiasis in Crohn's disease", International Journal of Urology (2009) 16, 477-480.
Jaghult, Susanna, et al., "Stress as a Trigger for Relapses in IBD: A Case-Crossover Study", Gastroenterology Research • 2013;6(1):10-16.
Jansson, Janet, et al., "Metabolomics Reveals Metabolic Biomarkers of Crohn's Disease", PLoS ONE Jul. 2009 | vol. 4 | Issue 7 | e6386, 10 pgs.
Jelenova, Daniela, et al., "Heart rate variability in children with inflammatory bowel diseases", Neuroendocrinology Letters vol. 36 No. 1 2015, 8 pgs.
Jones, Jennifer, et al., "Relationships Between Disease Activity and Serum and Fecal Biomarkers in Patients With Crohn's Disease", Clinical Gastroenterology and Hepatology 2008,6:1218-1224.

(56) References Cited

OTHER PUBLICATIONS

Kinnucan, Jami A., et al., "Sleep and Inflammatory Bowel Disease: Exploring the Relationship Between Sleep Disturbances and Inflammation", Gastroenterology & Hepatology vol. 9, Issue 11 Nov. 2013, 718-721.
Kuna, Andrea Tešija, "Serological markers of inflammatory bowel disease", Biochemia Medica 2013;23(1):28-42.
Limbergen, Johan Van, et al., "The Genetics of Crohn's Disease", Annu. Rev. Genomics Hum. Genet. 2009. 10:89-116.
Liu, Jimmy Z., et al., "Genetic studies of Crohn's disease: Past, present and future", Best Practice & Research Clinical Gastroenterology 28 (2014) 373-386.
Mahida, Y.R., et al., "High circulating concentrations of interleukin-6 in active Crohn's disease but not ulcerative colitis", Gut, 1991,32, 1531-1534.
Mishkin, Daniel, et al., "The Glucose Breath Test A Diagnostic Test for Small Bowel Stricture(s) in Crohn's Disease", Digestive Diseases and Sciences, vol. 47, No. 3 (Mar. 2002), pp. 489-494 (© 2002).
Nancey, S., et al., "Urinary Neopterin Is a Valuable Tool in Monitoring Crohn's Disease Activity", Inflamm Bowel Dis ? vol. 14, No. 11, Nov. 2008, 1548-1554.
Pelli, Maria Antonietta, et al., "Breath Mkanes Determination in Ulcerative Colitis and Crohn's Disease", Dis Colon Rectum, Jan. 1999;42:71-76.
Piras, C., et al., "Serum protein profiling of early and advanced stage Crohn's disease", EuPA Open Proteomics 3 (2 0 1 4) 48-59.
Rejchrt, S., et al., "Antilaminaribioside and Antichitobioside Antibodies in Inflammatory Bowel Disease", Folia Microbiol. 53 (4), 373-376 (2008).
Roma, E., et al., "Retinol Binding Protein 4 in children with Inflammatory Bowel Disease: a negative correlation with the disease activity", Hippokratia 2012, 16, 4: 360-365.
Szczeklik, Katarzyna, et al., "Proinflammatory cytokines in the saliva of patients with active and nonactive Crohn's disease", Polskie Archiwum Medycyny Wewnetrznej 2012; 122 (5), 200-208.
Vermeire, S., et al., "Laboratory Markers in IBD: Useful, Magic, or Unnecessary Toys?", Gut 2006;55:426-431.
Vrabie, Raluca, et al., "Noninvasive Markers of Disease Activity in Inflammatory Bowel Disease", Gastroenterology & Hepatology vol. 10, Issue Sep. 9, 2014, 576-584.
Walton, C., et al., "Analysis of Volatile Organic Compounds of Bacterial Origin in Chronic Gastrointestinal Diseases", Inflamm Bowel Dis vol. 19, No. 10, Sep. 2013, 2069-2078.
Wright, Emily K., et al., "Fecal Biomarkers in the Diagnosis and Monitoring of Crohn's Disease", Inflamm Bowel Dis 2014;20:1668-1677.
Zholudev, A., et al., "Serologic testing with ANCA, ASCA, and anti-OmpC in children and young adults with Crohn's disease and ulcerative colitis: diagnostic value and correlation with disease phenotype", American Journal of Gastroenterology. 99(11), 2235-2241.
Zimmermann, Ellen M., et al., "Magnetic resonance imaging of the small bowel in patients with Crohn's disease", Curr Opin Gastroenterol. Mar. 2011; 27(2), 12 pgs.
"European Application Serial No. 18822534.6, Response to Communication Pursuant to Rules 161 and 162 filed Dec. 22, 2020", 13 pgs.
"International Application Serial No. PCT/US2018/060622, International Preliminary Report on Patentability dated Jun. 4, 2020", 10 pgs.
"International Application Serial No. PCT/US2018/060622, International Search Report dated Feb. 12, 2019", 5 pgs.
"International Application Serial No. PCT/US2018/060622, Written Opinion dated Feb. 12, 2019", 8 pgs.
Jeffrey, Hyams, et al., "Evaluation of the Pediatric Crohn Disease Activity Index: A Prospective Multicenter Experience", Journal Of Pediatric Gastroenterology And Nutrition, vol. 41, No. 4, (Oct. 1, 2005), 416-421.
Michael, Bates D, "Pediatric Crohn's Disease Activity Index Calculator—Cincinnati Children's Hospital Medical Center", XP055550405, (Apr. 22, 2016).
Pellissier, S, et al., "Psychological adjustment and autonomic disturbances in inflammatory bowel diseases and irritable bowel syndrome", Psychoneuroendocrinology, Oxford, GB, vol. 35, No. 5, (Jun. 1, 2010), 653-662.
Turner, et al., "Development, Validation, and Evaluation of a Pediatric Ulcerative Colitis Activity Index: A Prospective Multi center Study", Gastroenterology, W.B. Saunders Co, US, vol. 133, No. 2, (Aug. 3, 2007), 423-432.
Vives-Boix, Victor, et al., "A Knowledge-Based Clinical Decision Support System for Monitoring Chronic Patients", International Conference On Simulation, Modeling, And Programming For Autonomous Robots,Simpar 2010; [Lecture Notes In Computer Science; Lect.Notes Computer], Springer, Berlin, Heidelberg, (May 27, 2017), 435-443.

* cited by examiner

ID
METHOD AND APPARATUS FOR MONITORING STATE OF INFLAMMATORY BOWEL DISEASE

CLAIM OF PRIORITY

This application claims the benefit of priority under 35 U.S.C. § 119(e) of U.S. Provisional Patent Application Ser. No. 62/590,307, filed on Nov. 23, 2017, which is herein incorporated by reference in its entirety.

TECHNICAL FIELD

This document relates generally to medical devices and more particularly to a system for monitoring and treating inflammatory bowel disease (IBD).

BACKGROUND

Over 1.4 million people in the United States suffer from Ulcerative Colitis and Crohn's Disease, collectively referred to as Inflammatory Bowel Disease (IBD). Patients with IBD require more frequent hospital admissions, with a longer length of stay and increased costs, than patients without IBD. Moreover, 30-day readmission rates for patients with IBD have been reported to be as high as 25%. Hospitalizations are an enormous burden to the affected individuals and to the healthcare system.

Researchers have been studying IBD to determine biomarkers of this disease for many years. Despite research revealing promising measures that have a correlation with disease status in recent years, including clinical variables, serological markers, fecal markers and genetic tests, none of these is predictive when being used alone, and no continuous monitoring solution exists for patients today.

IBD is characterized by bouts of inflammation. Studies have shown that a correlation exists between inflammatory markers and autonomic tone markers. In a study of Crohn's Disease (CD) patients with age- and gender-matched controls, the CD subjects had significantly higher levels of inflammatory markers CRP and IL-6 compared to controls. Further, it was demonstrated that Heart Rate Variability (HRV) values of very-low-frequency power and low-frequency power components were significantly lower in CD subjects, implying a predominant sympathetic tone. Other studies have shown similar correlations between inflammatory markers and autonomic tone in IBD and other populations. Still other studies have shown a correlation between stress and/or sleep disturbances and disease relapses. A review publication of many studies concluded intestinal inflammatory processes reduce the absorption of sodium, chloride and calcium, while they increase potassium secretion. In addition, mild to severe metabolic alkalosis may occur in IBD patients, mainly depending on the severity of the disease and the part of the gastrointestinal tract being affected.

SUMMARY

An Example (e.g., "Example 1") of a system for monitoring and treating a medical condition of a patient may include signal inputs, a signal processing circuit, and a medical condition analyzer. The signal inputs may be configured to receive patient condition signals indicative of a state of inflammatory bowel disease (IBD). The signal processing circuit may be configured to process the received patient condition signals and to generate patient condition parameters using the processed patient condition signals. The patient condition parameters are indicative of the state of IBD. The medical condition analyzer may be configured to determine the medical condition of the patient using the generated patient condition parameters. The medical condition analyzer may include a physiological marker input, a quality of life input, and a parameter analysis circuit. The physiological marker input may be configured to receive one or more physiological marker parameters of the patient condition parameters. The one or more physiological marker parameters are each representative of a physiological marker of IBD. The quality of life input may be configured to receive one or more quality of life parameters of the patient condition parameters. The one or more quality of life parameters are each a measure of quality of life of the patient. The parameter analysis circuit may be configured to analyze the received patient condition parameters and determine the medical condition including the state of IBD using an outcome of the analysis.

In Example 2, the subject matter of Example 1 may optionally be configured to further include a therapy device configured to deliver one or more therapies treating IBD and a control circuit configured to control the delivery of the one or more therapies based on the determined medical condition.

In Example 3, the subject matter of any one or any combination of Examples 1 and 2 may optionally be configured such that the parameter analysis circuit is configured to produce a patient condition metric being a linear or nonlinear combination of at least two parameters of the received patient condition parameters and to determine the medical condition based on the medical condition metric.

In Example 4, the subject matter of any one or any combination of Examples 1 to 3 may optionally be configured such that the medical condition analyzer includes an notification circuit configured to produce one or more medical condition indicators based on the determined medical condition and output the one or more medical condition indicators. The one or more medical condition indicators indicate at least an instant state of IBD.

In Example 5, the subject matter of Example 4 may optionally be configured to further include a storage device configured to store the determined medical condition, and such that the analysis circuit is further configured to produce and analyze a trend of the state of IBD, and the notification circuit is configured to detect changes in the medical condition from the trend of the state of IBD and to produce the one or more medical condition indicators to further indicate one or more of the trend of the state of IBD or the detected changes in the medical condition.

In Example 6, the subject matter of any one or any combination of Examples 4 and 5 may optionally be configured such that the notification circuit is configured to detect a need for intervention from the determined medical condition and to generate an alert or notification of the one or more medical condition indicators in response to a detection of the need for intervention.

In Example 7, the subject matter of any one or any combination of Examples 4 to 6 may optionally be configured such that the notification circuit is configured to classify the patient with respect to a risk of exacerbation of IBD based on the one or more medical condition indicators and to produce the one or more medical condition indicators to further indicate the classification.

In Example 8, the subject matter of any one or any combination of Examples 1 to 7 may optionally be configured such that the medical condition analyzer further includes a chemical marker input configured to receive one or more chemical marker parameters of the patient condition parameters. The one or more chemical marker parameters are each representative of a chemical marker of IBD.

In Example 9, the subject matter of any one or any combination of Examples 1 to 8 may optionally be configured such that the medical condition analyzer further includes an environmental information input configured to receive one or more environmental parameters of the patient condition parameters, the one or more environmental parameters indicative of an environment of the patient.

In Example 10, the subject matter of any one or any combination of Examples 1 to 9 may optionally be configured such that the medical condition analyzer further includes a trigger input configured to receive one or more triggering signals for adjusting the processing of the received patient condition signals.

In Example 11, the subject matter of any one or any combination of Examples 1 to 10 may optionally be configured such that the medical condition analyzer further includes an external information input configured to receive external information including at least information from the medical record of the patient, and the parameter analysis circuit is configured to analyze the received patient condition parameters with the received external information.

In Example 12, the subject matter of any one or any combination of Examples 1 to 11 may optionally be configured to further include one or more sensors configured to sense one or more signals related to the medical conditions and to produce one or more sensor signals of the patient condition signals.

In Example 13, the subject matter of Example 12 may optionally be configured to include an implantable medical device including at least the signal inputs, the signal processing circuit, and the medical condition analyzer, and configured such that the one or more sensors include one or more implantable sensors.

In Example 14, the subject matter of Example 12 may optionally be configured such that the one or more sensors include one or more non-implantable sensors.

In Example 15, the subject matter of Example 12 may optionally be configured such that the one or more sensors include at least one implantable sensor.

An example (e.g., "Example 16") of a method for monitoring and treating a medical condition of a patient is also provided. The method may include receiving patient condition signals indicative of a medical condition including a state of inflammatory bowel disease (IBD), generating patient condition parameters indicative of the medical condition including the state of IBD using the processed patient condition signals, and determining the medical condition including the state of IBD by analyzing the generated patient condition parameters. The patient condition parameters may include at least one or more physiological marker parameters and one or more quality of life parameters. The one or more physiological marker parameters are each representative of a physiological marker of IBD. The one or more quality of life parameters are each a measure of quality of life of the patient.

In Example 17, the subject matter of Example 16 may optionally further include delivering one or more therapies treating IBD and controlling the delivery of the one or more therapies based on the determined medical condition.

In Example 18, the subject matter of determining the medical condition as found in any one or any combination of Examples 16 and 17 may optionally further include producing a patient condition metric being a linear or nonlinear combination of at least two parameters of the received patient condition parameters, and determining, using the patient condition metric, one or more of: an instant state of IBD, a trend of the state of IBD, a change in the medical condition a need for intervention, or a classification of the patient with respect to a risk of exacerbation of IBD.

In Example 19, the subject matter of generating the patient condition parameters as found in any one or any combination of Examples 16 to 18 may optionally further include generating one or more chemical marker parameters each representative of a chemical marker of IBD.

In Example 20, the subject matter of generating the patient condition parameters as found in any one or any combination of Examples 16 to 19 may optionally further include generating one or more environmental parameters indicative of an environment of the patient.

In Example 21, the subject matter of any one or any combination of Examples 16 to 20 may optionally further include receiving one or more triggering signals and adjusting the generation of the patient condition parameters in response to receiving the one or more triggering signals.

In Example 22, the subject matter of any one or any combination of Examples 16 to 20 may optionally further include receiving external information including at least information from the medical record of the patient, and the subject matter of determining the medical condition including the state of IBD as found in any one or any combination of Examples 16 to 20 may optionally further include analyzing the generated patient condition parameters with the received external information.

In Example 23, the subject matter of any one or any combination of Examples 16 to 20 may optionally further include sensing one or more signals related to the medical conditions and producing one or more sensor signals of the patient condition signals using one or more sensors.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, methods and systems for monitoring inflammatory bowel disease (IBD) patients. There is a clinical need for monitoring IBD patients to provide an early prediction of an impending relapse of disease, so that they can seek medical care, take pharmaceutical agents, and/or make daily lifestyle changes to avoid a visit to an emergency room and/or hospitalization.

The present system provides for monitoring IBD and similar inflammatory disorders to provide a reliable marker of a patient's condition and to detect (1) worsening symptoms, to warn the patient and provide a window to administer therapy to prevent hospitalizations, and (2) exacerbations (also referred to as flares), to alert appropriate medical personnel of the rapid onset of symptoms to provide the patient with the needed medical care. The present system can also use results of the detection as an input to a system for administering therapy, such as in a closed-loop therapy system (e.g., a drug delivery system or a neurostimulation system). In various embodiments, the present system can measure and use physiological markers that correlate with autonomic tone for IBD monitoring. Importantly, many patients have reported varying pre-exacerbation symptoms (e.g., feeling of fatigue, sensations in the mouth, stomach sounds, etc., though varying from patient to patient), often days in advance of the exacerbation, thus offering opportunity for early detection (an "intervention window"). In various embodiments, the present system can receive information such as data from sensors assessing patient status, patient and/or caregiver input, and environmental conditions and use such information to improve the outcome of IBD monitoring and onset prediction.

Figure 1:
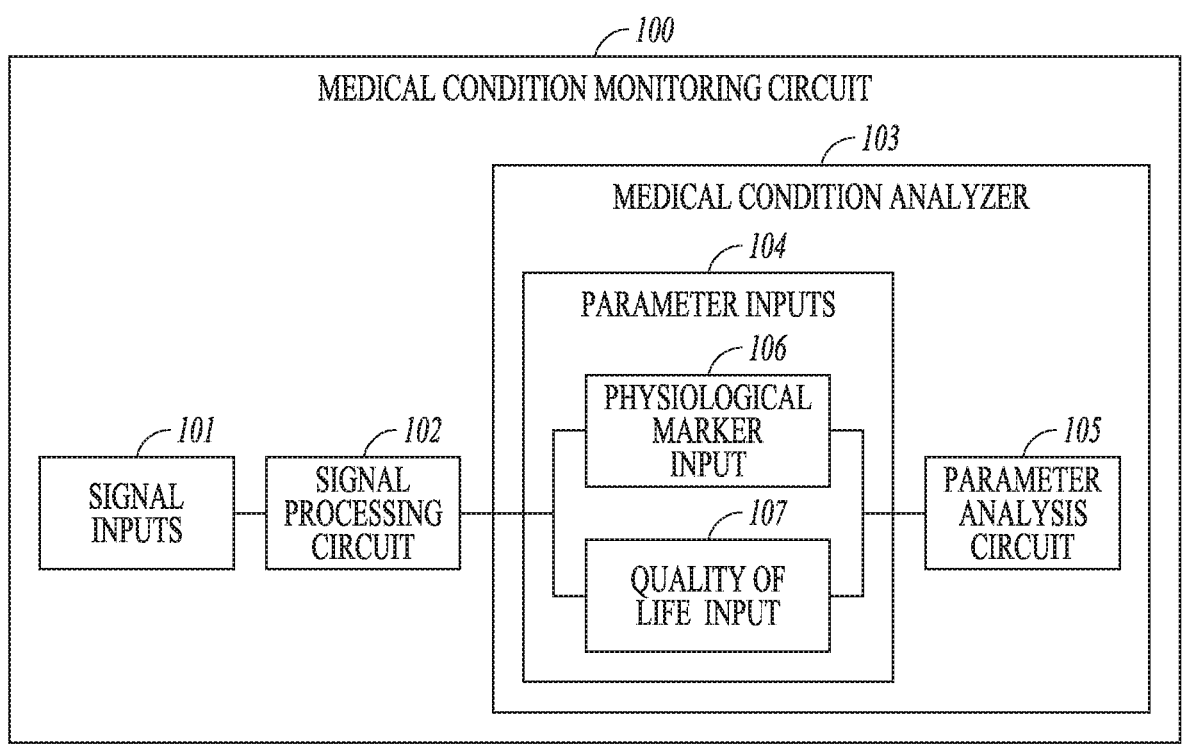
FIG. 1 illustrates an embodiment of a circuit for monitoring a medical condition of a patient.

The present system can be non-invasive, non-implantable, partially implantable, or fully implantable. The system can include one or more sensors to indirectly or directly measure the patient's symptoms and/or physiological signals indicative of worsening condition and/or onset of an exacerbation. The system can also include a processing unit to process incoming signals and execute an algorithm using the processed signals along with stored data (e.g., trend data) to assess the patient's condition. In the event of worsening symptoms preceding or at the onset of an exacerbation, the system can notify the patient and/or a user, and/or start or adjust a therapy. In this document, a "user" can include a physician, other medical professional, or caregiver who attends the patient including monitoring and/or treating the patient using the present system FIG. 1 illustrates an embodiment of a medical condition monitoring circuit 100 for monitoring medical condition including IBD in a patient. Medical condition monitoring circuit 100 can include signal inputs 101, signal processing circuit 102, and a medical condition analyzer 103. In various embodiments, medical condition monitoring circuit can be implemented as part of a system for monitoring and/or treating the patient.

Signal inputs 101 can receive patient condition signals indicative of a state of IBD. Signal processing circuit 102 can process the received patient condition signals and generate patient condition parameters using the processed patient condition signals. The patient condition parameters are indicative of the state of IBD. Medical condition analyzer 103 can determine the medical condition of the patient using the generated patient condition parameters, and can include parameter inputs 104 and parameter analysis circuit 105. Parameter inputs 104 receive the patient condition parameters, and can include a physiological marker input 106 and a quality of life parameter input 107. Physiological marker input 104 can receive one or more physiological marker parameters of the patient condition parameters. The one or more physiological marker parameters can each be representative of a physiological marker of IBD. Quality of life input 107 can receive one or more quality of life parameters of the patient condition parameters. The one or more quality of life parameters are each a measure of quality of life of the patient. Parameter analysis circuit 105 can analyze the received patient condition parameters and determine the medical condition including the state of IBD using an outcome of the analysis.

Figure 2:
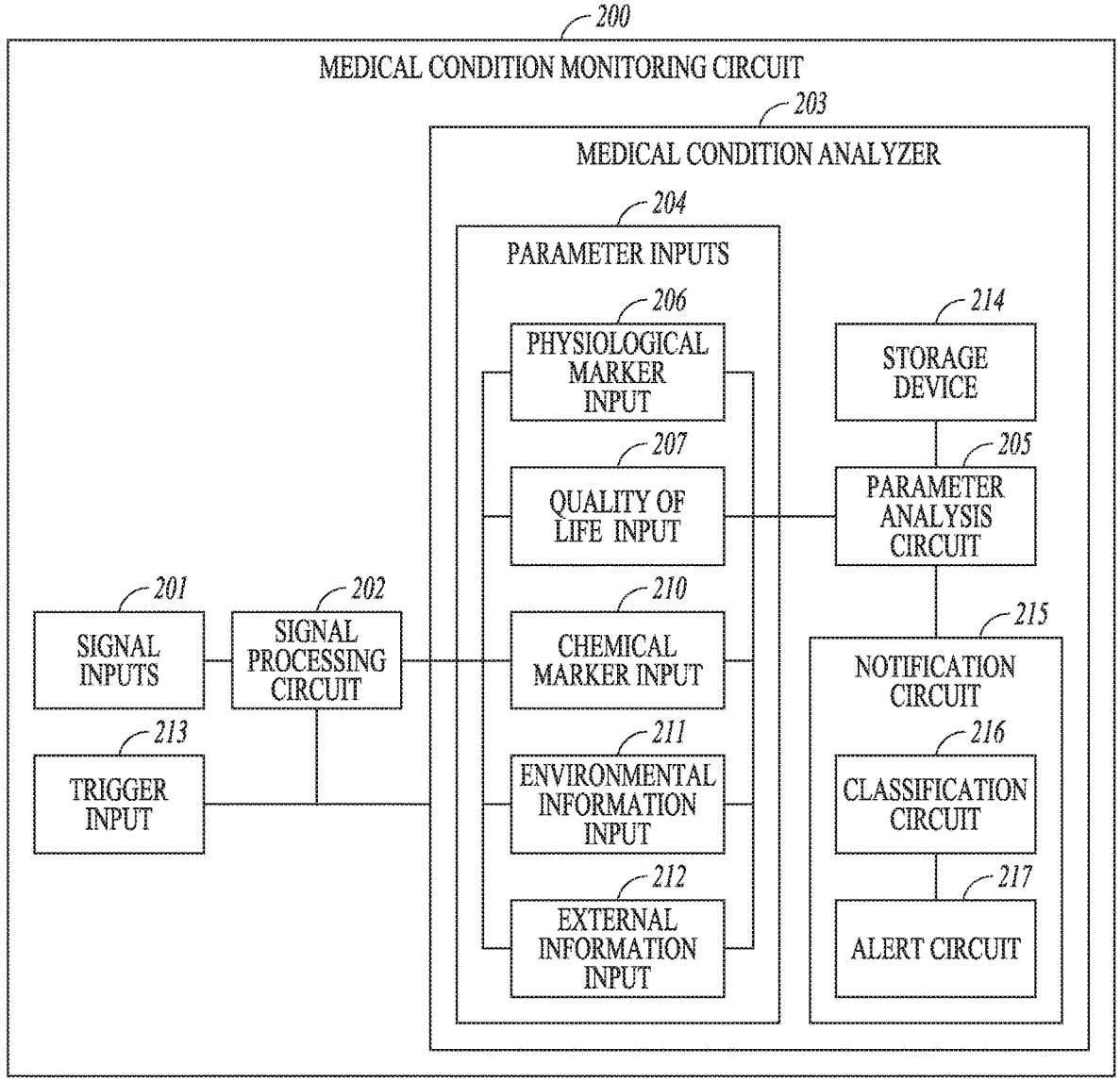
FIG. 2 illustrates an embodiment of another circuit for monitoring the medical condition of a patient.

FIG. 2 illustrates an embodiment of a medical condition monitoring circuit 200, which can represent an example of medical condition monitoring circuit 100. Medical condition monitoring circuit 200 can include signal inputs 201, a signal processing circuit 202, a trigger input 213, and a medical condition analyzer 203.

Signal inputs 201 can represent an example of signal inputs 101 and can receive the patient condition signals indicative of the medical condition including the state of IBD. The patient condition signals can include one or more sensor signals produced by sensors. In various embodiments, the patient condition signals can also include other (non-sensor) signals related to determination of the state of IBD. Examples of such non-sensor signals can include data manually entered by the patient, data manually entered by the user, and data extracted from an electronic medical record.

Signal processing circuit 202 can represent an example of signal processing circuit 102 and can process the received patient condition signals and generate patient condition parameters using the processed patient condition signals. The patient condition parameters can be indicative of the medical condition including the state of IBD. The patient condition parameters can each be a single parameter (e.g., a parameter directly measured from a patient condition signal) or a parameter metric being a linear or nonlinear combination of two or more parameters (e.g., a parameter determined as a function of two or more parameters each directly measured from a patient condition signal).

Trigger input 213 can receive one or more triggering signals for adjusting the sensing and the processing of the patient condition signals by medical condition monitoring circuit 200. The one or more triggering signals indicate when the patient condition signals can be received for monitoring the patient's medical condition including the state of IBD and/or how the patient condition signals should be processed (e.g., using need-based sampling rates). In various embodiments, the one or more trigger signals can also be used to activate and inactivate various sensors and/or other sources of the patient condition signals. Examples of the one or more triggering signals include an activity signal indicative of the patient's activity level and/or a sleep signal indicative of whether the patient is sleeping. The one or more triggering signals can be sensed from the patient using one or more sensors (e.g., activity sensor and/or sleep sensor), and/or using other information such as time of the day and/or patient input. In various embodiments, the one or more triggering signals can allow for power conservation. When medical condition monitoring circuit 200 is implemented in a battery-operated system, battery life can be extended by activating certain sensors and/or maintaining a high sampling rate only as needed. In various embodiments, the one or more triggering signals can enhance the detection of the patient's medical condition including the state of IBD. Higher-frequency sampling for certain patient condition signals (e.g., signals indicative of heart sounds and/or respiratory sinus arrhythmia) may be triggered only during rest and/or sleep to reduce unwanted signals related to the patient's physical activities. A "clean" signal may facilitate IBD detection of detect early signs of exacerbation of IBD several days in advance. Higher-frequency sampling for the certain patient condition signals may also be triggered during high-risk times (e.g., based on a time of day, week, month, or year, or based on a cycle learned from the patient's previous symptoms and/or exacerbations by executing an algorithm in medical condition monitoring circuit 200).

Medical condition analyzer 203 can represent an example of medical condition analyzer 103 and can determine the medical condition including the IBD of the patient using the generated patient condition parameters. Medical condition analyzer 203 can include parameter inputs 204, a parameter analysis circuit 205, a storage device 214, and a notification circuit 215. Parameter inputs 204 can represent an example of parameter inputs 104 and can receive the patient condition parameters. In the illustrated embodiment, parameter input 204 includes a physiological marker input 206, a quality of life input 207, a chemical marker input 210, an environmental information input 211, and an external information input 212. In various embodiments, parameter input 204 can include any one or any combination of (a) physiological marker input 206, (b) quality of life input 207, (c) chemical marker input 210, (d) environmental information input 211, and (e) external information input 212. For example, depending on the need and/or available of the patent condition signals, parameter input 204 can include (a), (ab), (ac), (ad), (ae), (abc), (abd), (abe), (acd), (ace), (ade), (abcd), (abce), (abde), or (abcde).

Physiological marker input 206 can represent an example of physiological marker input 106 and can receive one or more physiological marker parameters each represents a physiological marker of IBD. In various embodiments, the one or more physiological marker parameters can include any one or any combination of the following:

(i) Heart rate, generated by signal processing circuit 202 using one or more cardiac signals sensed by one or more cardiac sensors such as electrocardiogram (ECG) sensor (including surface, subcutaneous, and/or intracardiac electrodes), accelerometer, gyroscope, electrical bioimpedance sensor, impedance cardiograph sensor, optical sensor, radiowave sensor, and/or microwave sensor.

(ii) Heart rate variability (HRV) parameter(s), generated by signal processing circuit 202 using the one or more cardiac signals as discussed for (i) above. Examples of HRV parameters include standard deviation of normal-to-normal intervals (SDNN), standard deviation of averages of normal-to-normal intervals (SDANN), high-frequency HRV (HF-HRV), low-frequency HRV (LF-HRV), ratio of low-frequency (LF) to high-frequency (HF) HRV (LF/HF ratio), HRV footprint, root-mean-square successive differences (RMSSD), and percentage of differences between normal-to-normal intervals that are greater than 50 milliseconds (pNN50).

(iii) Heart rate acceleration and deceleration capacity parameter(s), generated by signal processing circuit 202 using the one or more cardiac signals as discussed for (i) above.

(iv) ECG morphology parameter(s), generated by signal processing circuit 202 using one or more ECG signals sensed using one or more cardiac sensors such as ECG sensor (including surface, subcutaneous, and/or intracardiac electrodes).

(v) Respiration rate, generated by signal processing circuit 202 using one or more respiratory signals (each being a signal indicative of the respiration rate) sensed using one or more respiratory sensors such as ECG sensor (including surface, subcutaneous, and/or intracardiac electrodes), accelerometer, gyroscope, and/or electrical bioimpedance sensor (for sensing transthoracic impedance.

(vi) Respiration-mediated cardiac parameter(s), including sinus arrhythmia (RSA) parameter(s), generated by signal processing circuit 202 using the one or more cardiac signals as discussed in (i) above and the one or more respiratory signals as discussed in (v) above.

(vii) Blood pressure or a surrogate of blood pressure parameter(s), generated by signal processing circuit 202 using one or more blood pressure signals sensed using one or more blood pressure sensors such as accelerometer (for sensing heart sounds as an indirect measure of blood pressure using the second heart sound, S2), pressure sensor, the ECG sensor, photoplethysmography (PPG) sensor (for pulse transit time, pulse amplitude, normalized pulse volume, etc.), electrical bioimpedance sensor (for pulse transit time), and/or impedance cardiography sensor.

(viii) Blood flow and/or blood volume pulse parameter(s), generated by signal processing circuit 202 using one or more blood flow signals (each indicative of a blood flow rate or blood volume pulse) sensed by one or more blood flow sensors such as PPG sensor, electrical bioimpedance sensor, and/or impedance cardiography sensor.

(ix) Blood pressure variability, blood flow variability, and/or blood volume pulse variability parameter(s), generated by signal processing circuit 202 using one or more blood pressure signals as discussed in (viii) and/or the one or more blood flow signals as discussed in (ix) above.

(x) Blood pressure morphology, blood flow morphology, and/or blood volume pulse morphology parameter(s), generated by signal processing circuit 202 using one or more blood pressure signals as discussed in (viii) and/or the one or more blood flow signals as discussed in (ix) above.

(xi) Baroreceptor response parameter(s), including baroreceptor reflex sensitivity, generated by signal processing circuit 202 using one or more cardiac signals as discussed in (i) and/or the one or more blood pressure signals as discussed in (vii) above, paired with one or more of activity, posture, or respiration signal (e.g., to capture baroreceptor reflex sensitivity).

(xii) Heart sound parameter(s) (measures of the first, second, third, and/or fourth heart sounds, S1, S2, S3, and/or S4, respectively), generated by signal processing circuit 202 using one or more heart sound signals sensed by one or more heart sound sensors such as accelerometer and acoustic sensor (e.g., microphone).

(xiii) Heart sound variability parameter(s) (e.g. amplitude variability), generated by signal processing circuit 202 using one or more heart sound signals as discussed in (xii) above.

(xiv) Galvanic skin response and/or electrodermal activity parameter(s), generated by signal processing circuit 202 using one or more electrical conductance signals sensed by one or more skin conductance sensors.

(xv) Temperature, generated by signal processing circuit 202 using one or more temperature signals sensed by one or more temperature sensors.

(xvi) Gut pressure and/or gut sound parameter(s), generated by signal processing circuit 202 using one or more gut pressure and/or gut sound signals sensed by gut pressure and/or gut sound sensors such as accelerometer and/or acoustic sensor.

(xvii) Any parameter(s) selected from (i)-(xvi) above measured as a function of posture, activity level, sleep/awake status, and or external environmental factors such as temperature and/or altitude. This can be important because, for example, with a sleep sensor, autonomic tone measures (e.g., (i)-(xv) above, among other sympathetic and/or parasympathetic nervous system markers) can only be assessed during nighttime, when other factors that influence autonomic tone, such as activity level, are constant. The 'noise' in the signals is also reduced substantially at night. In various embodiments, the one or more physiological marker parameters are generated using the one or more patient condition signals sensed at nighttime. Nighttime is considered to be an opportunity (though not the only time) for assessing the patient's medical condition including the state of IBD under constant and/or known conditions. During other times when the patient may be active, more factors may need to be considered to avoid misleading results. For example, a change in activity level may cause a threshold for sympathetic tone to be adjusted, which in turn may result in false detection of exacerbation. Thus, for example, quality of life parameters (as discussed below) may be needed as the factors for avoiding misleading results. In addition, measures of autonomic tone can be acquired during known movements or instructions given to the patient. For example, if a type of physical movement is known to result in a certain response of the autonomic nervous system, this type of movement can be used as a constant state or known state for assessing the patient's medical condition.

Quality of life input 207 can represent an example of quality of life input 107 and can receive one or more quality of life parameters each being a measure of quality of life of the patient. In various embodiments, the one or more quality of life parameters can include any one or any combination of the following:

(i) Activity level(s), generated by signal processing circuit 202 using one or more activity signals sensed by one or more activity sensors such as accelerometer, gyroscope, and/or globe positioning system (GPS) sensor.

(ii) Sleep duration, depth of sleep, and/or number of awakenings, generated by signal processing circuit 202 using one or more sleeping signals sensed by one or more sleeping sensors such as accelerometerr, gyroscope, ECG sensor, temperature, sensor, and/or blood pressure sensor.

(iii) Stress level(s), generated by signal processing circuit 202 by driving from any one or any combination of the physiological markers parameters (i)-(xvii) above and/or input from the patient.

(iv) Pain or discomfort level(s), generated by signal processing circuit 202 using one or more signals providing for an objective measure of pain. Examples of such objective measures of pain is discussed in U.S. patent application Ser. No. 15/688,676, entitled "METHOD AND APPARATUS FOR PAIN MANAGEMENT USING OBJECTIVE PAIN MEASURE", filed on Aug. 28, 2017, assigned to Boston Scientific Neuromodulation Corporation, which is incorporated by reference herein in its entirety.

Chemical marker input 210 can receive one or more chemical marker parameters each representative of a chemical marker of IBD. In various embodiments, the one or more chemical marker parameters can include any one or any combination of the following:

(i) Inflammation marker parameter(s), generated by signal processing circuit 202 using one or more inflammation marker signals sensed by one or more chemosensors sensing levels of one or more chemical markers of inflammation (e.g., one or more measures of TNF-alpha, C-reactive protein, erythrocyte sedimentation rate, plasma viscosity, and/or Interleukin-2 receptor).

(ii) Stress marker parameter(s), generated by signal processing circuit 202 using one or more stress marker signals sensed by one or more chemosensors sensing levels of one or more chemical markers of stress (e.g., cortisol, and/or prolactin).

(iii) Electrolyte level parameter(s), generated by signal processing circuit 202 using one or more electrolyte signals sensed by one or more chemosensors sensing levels of one or more electrolytes (e.g., potassium and/or sodium).

(iv) pH value, generated by signal processing circuit 202 using one or more pH signals sensed by one or more pH sensors.

Environmental information input 211 can receive one or more environmental parameters indicative of an environment of the patient. In various embodiments, the one or more environmental parameters can include any one or any combination of time of day, time of month, time of year, GPS location, pollen levels, pollution levels, temperature, humidity levels, ultraviolet (UV) levels, web information on local news, and/or hospital admissions. The one or more environmental parameters can be generated by signal processing circuit 202 using one or more sensor signals, patient and/or user input, and/or signals from other sources.

External information input 212 can receive one or more external information parameters related to health of the patient. The one or more external information parameters can be generated by signal processing circuit 202 using one or more sensor signals, patient and/or user input, and/or signals from other sources. In various embodiments, the one or more external information parameters can include any one or any combination of the following:

(i) Demographic data, such as age, gender, race, smoking status, age of disorder onset, duration of disorder, and/or family medical history.

(ii) Electronic personal and/or medical data, such as prior exacerbation and relapse information, drugs (e.g., NSAIDs, antibiotics, hormone replacement therapy drugs, oral contraceptive pills, and/or cyclooxygnase-2), prior surgeries (e.g. appendectomy), comorbidities, and/or mental health.

(iii) Secondary test data, such as gut microbiota, genomics, serological antibody markers, serological inflammatory markers (e.g., C-reactive protein, erythrocyte sedimentation rate (ESR), interleukin (IL)-1 Beta, IL-2, IL-6, IL-8, IL-10, IL-16, IL-2 soluble receptor, tumor necrosis factor-alpha (TNF-alpha), TNF-alpha soluble receptor, and/or IFN-gamma), white blood cell count, Intestinal permeability, endoscopy results (e.g., mucosal healing, confocal laser endomicroscopy, and/or magnifying colonoscopy), histology results, fecal markers (e.g., fecal calprotectin, lactoferrin, S100A12, indium 111-labeled leukocytes, alpha1-antitrypsin, alpha2-macroglobulin, myeloperoxidase, and PMNelastase).

(iv) Time of day, week, month, and/or year.

(v) Environmental data, such as temperature, air quality, location, and/or humidity.

(vi) Patient input, such as patient diary data (e.g., records of diet, bowel movements, and/or medication adherence) and/or alert or emergency call by the patient (e.g., by pressing a button when not be feeling well). The patient's alert or emergency call can in combination with other parameters can lead to medical intervention, and can be used as a command to adjust signal processing (e.g., start sensing certain signals or increasing sampling rate).

(vii) Other data such as disease location, socioeconomic status, major life events, social media feeds, and/or internet searches.

(viii) Dietary and/or pharmaceutical information.

(ix) Any one of the physiological marker parameters discussed above in combined with at least one of the external information parameters (i)-(vii) above.

Parameter analysis circuit 205 can represent an example of parameter analysis circuit 105 and can analyze the received patient condition parameters and determine the patient's medical condition including the state of IBD using an outcome of the analysis. In various embodiments, parameter analysis circuit 205 can produce a patient condition metric using at least two patient condition parameters, such as a physiological marker parameter and a quality indicator parameter. The patient condition metric can be a linear or nonlinear combination of the patient condition parameters. In various embodiments, the patient condition metric can be an IBD status metric that allow for detection of the state of the IBD. In some embodiments, the patient condition metric can also be used to indicate or detect one or more other inflammatory and/or other disorders. In one embodiment, parameter analysis circuit 205 executes an IBD algorithm for determining the state of IBD, including predicting exacerbation or relapse.

Storage device 214 can store results of the analysis of the patient condition parameters. In addition to presenting the results to the user, the stored information can allow parameter analysis circuit 205 to produce and analyze a trend of the medical condition, such as a trend of the state of the IBD. This allows for monitoring progress of the medical condition including the state of IBD of the patient over time, and allows for identification of changes in the medical condition of the patient from the trend.

Notification circuit 215 can produce one or more medical condition indicators using results of the analysis performed by parameter analysis circuit 205. Such one or more medical condition indicators can indicate, for example, an instant state of IBD, a trend of the state of IBD, a classification of the IBD, and/or an alert or alarm for a worsening of the state of IBD or predicted exacerbation or relapse. In the illustrated embodiment, notification circuit 215 includes a classification circuit 216 and an alert circuit 217. Classification circuit 216 can classify the patient with respect to a risk of exacerbation based on the one or more medical condition indicators. Alert circuit 217 can detect a need for intervention from the results of the analysis performed by parameter analysis circuit 205 and can generate an alert or alarm in response to a detected of the need. The alert or alarm can include a notification indicating the patient's medical condition and can indicate a need for medical intervention. In various embodiments, alert circuit 217 can detect the need for intervention based on early or late stage of worsening symptoms and slow or rapid onset of IBD.

Figure 3:
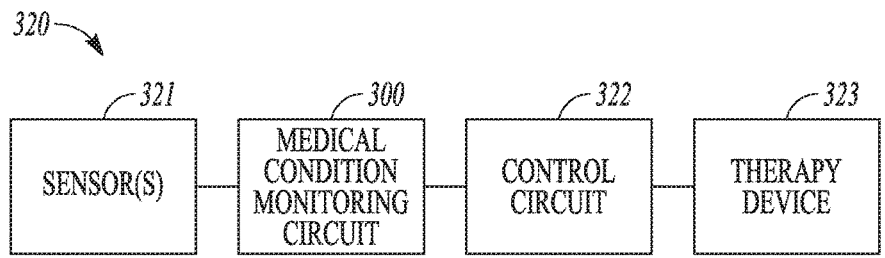
FIG. 3 illustrates an embodiment of system for monitoring and treating the medical condition, wherein the circuit of FIG. 1 or FIG. 2 may be used.

FIG. 3 illustrates an embodiment of system 320 for monitoring and treating the medical condition of the patient. Medical condition monitoring circuit 100 or 200 can be implemented in system 320. For monitoring purposes, system 320 includes at least one or more sensors 321 and a medical condition monitoring circuit 300. For monitoring and therapeutic purposes, system 320 can include sensor(s) 321, medical condition monitoring circuit 320, a control circuit 322, and a therapy device 323. Sensor(s) 321 can sense one or more signals related to the patient's medical condition including the state of IBD and produce the one or more sensor signals of the patient condition signals. Examples of sensor(s) 321 can include one or more of sensors selected from the sensors listed in Table 1. Therapy device 323 can deliver one or more therapies treating the detected medical condition. Example of the one or more therapies can include drug therapy and neuromodulation therapy (e.g., vagus nerve stimulation, peripheral nerve stimulation, sympathetic nerve stimulation, and/or sympathetic nerve inhibition). Control circuit 322 can control the delivery of the one or more therapies based on the medical condition as determined by medical condition monitoring circuit 300. Examples of medical condition monitoring circuit 300 include medical condition monitoring circuits 100 and 200. In addition to, or in place of, delivering the one or more therapies, system 320 can also recommend to the patient or the user actions to take based on the patient's medical condition including the state of IBD. In various embodiments, system 320 is a closed-loop therapy system, with sensor(s) 321 sensing effects of delivery of the one or more therapies for adjusting the delivery based on the effects.

In one embodiment, sensor(s) 321, medical condition monitoring circuit 300, control circuit 322, and therapy device 323 are integrated into a single medical device. In other embodiments, sensor(s) 321, medical condition monitoring circuit 300, control circuit 322, and therapy device 323 can be implemented as two or more medical devices communicatively coupled to each other to form system 320. These two or more devices can be any combination of implantable, wearable, handheld, and/or remote devices.

In various embodiments, sensor(s) 321 can include, but are not limited to, one or more sensors selected from the sensors discussed above in association with parameter inputs 204 and summarized in Table 1. As indicated in Table 1, sensor(s) 321 can include one or more implantable sensors configured to be placed within the patient and one or more non-implantable sensors to be placed on or near the patient. Examples of a non-implantable sensor can include non-body contacting sensor (or "no-contact sensor"), wearable sensor, mobile device, and adhesive patch. Table 1 indicates possible implementation of each sensor in one or more of such implantable and non-implantable configurations.

The no-contact sensor can be configured to be wirelessly coupled to the patient. The no-contact sensor can include, for example, one or more passive in-home monitors using radio or microwave signals or cameras (e.g., visible or infrared) to identify individuals and detect signals or metrics including, but not limited to, heart rate, heart rate variability, respiratory rate, respiratory-mediated heart rate, pulse transit time, surrogates of blood pressure, sleep duration, sleep quality, activity levels, posture, and/or measures of pain.

The wearable sensor can be configured to be worn by the patient. The wearable sensor can include wearable devices, including but not limited to wrist-wearables, rings, necklaces, earbuds, anklets, glasses, sensors embedded in clothing, and/or other non-fully implantable wearable devices capable of detecting signals and/or signal metrics including, but not limited to, sweat, saliva, urine, feces, other bodily fluids (for chemosensors), heart sounds, vocal expression, gut sounds, galvanic skin response, heart rate, heart rate variability, respiratory rate, respiratory-mediated heart rate, blood volume pulse, blood volume pulse variability, pulse transit time, blood pressure, surrogates of blood pressure, sleep duration, sleep quality, activity levels, posture, measures of pain, blood pressure and heart rate signals paired with one or more of activity, posture, or respiration signal to capture baroreceptor reflex sensitivity, and/or pulmonary airflow.

The mobile device can include a mobile device (e.g., smart phone) that is wirelessly coupled to one or more sensors and configured to receive signals from the one or more sensors intermittently, continuously, and/or as triggered by the user or the patient. Example of the received signals can include vocal expression, activity levels, heart rate, heart rate variability, respiration rate, respiratory sinus arrhythmia, sleep duration and/or sleep quality (e.g. when laying on bed beside patient, using 3-axis accelerometer), and/or heart sounds.

The adhesive patch can be configured to be attached to skin of the patient. Examples of the adhesive sensor can include electrodes and/or other sensors attached onto the skin using one or more adhesive pads or tapes and/or electronic tattoos capable of measuring any of the patient condition parameters.

The various sensors as discussed above in this document and summarized in Table 1 are presented by way of example, but not by way of restriction. Any types of sensors capable of producing the patient condition signals as discussed in this document can be used as sensor(s) 321.

In various embodiments, circuits of system 320, including its various embodiments discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
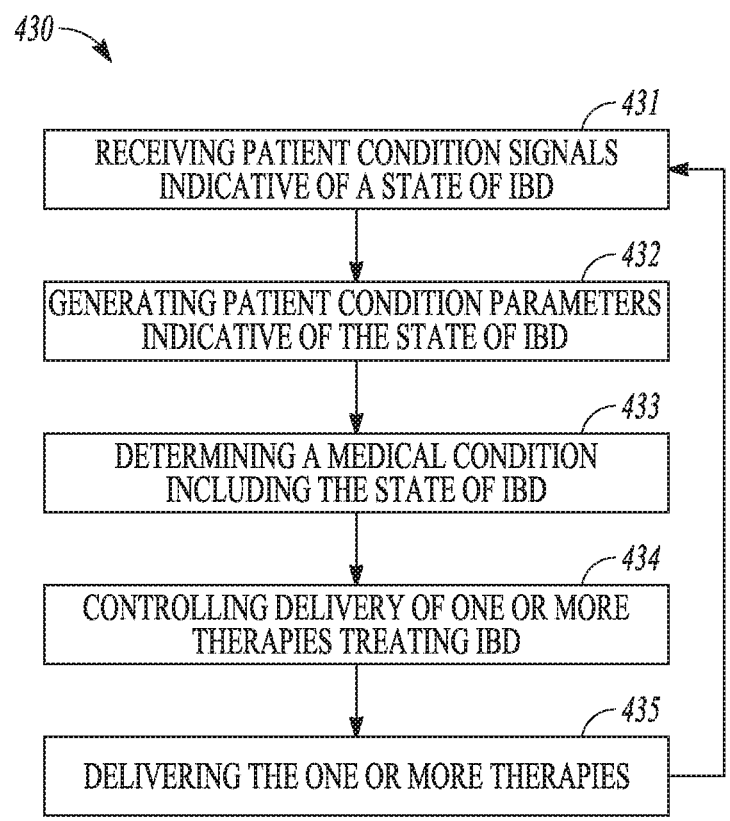
FIG. 4 illustrates an embodiment of a method for monitoring and treating a medical condition, such as may be performed by the system of FIG. 3.

FIG. 4 illustrates an embodiment of a method 430 for monitoring and treating a medical condition of a patient. Method 430 can be performed using system 320, including various embodiments of its components.

At 431, patient condition signals indicative of a medical condition including a state of IBD are received. In various embodiments, one or more sensors (e.g., selected from the sensors in Table 1) are used to sense one or more signals related to the medical conditions and produce one or more sensor signals each being one of the patient condition signals. The patient condition signals can also include signals from other devices or systems and/or information entered by the patient or the user.

At 432, patient condition parameters indicative of the medical condition including the state of IBD are generated using the processed patient condition signals. In various embodiments, the patient condition parameters include at least one or more physiological marker parameters and one or more quality of life parameters. The one or more physiological marker parameters are each representative of a physiological marker of IBD. The one or more quality of life parameters are each a measure of quality of life of the patient. In various embodiments, the patient condition parameters can also include one or more chemical marker parameters each representative of a chemical marker of IBD and/or one or more environmental parameters indicative of an environment of the patient. In various embodiments, one or more triggering signals; and the generation of the patient condition parameters is adjusted in response to reception the one or more triggering signals. The adjustment can include, for example, starting, stopping, and/or adjusting sampling rate for the generation of the patient condition parameters.

At 433, the medical condition including the state of IBD is determined by analyzing the generated patient condition parameters. In various embodiments, a patient condition metric is produced as a linear or nonlinear combination of at least two parameters of the received patient condition parameters (e.g., a physiological marker parameter and a quality of life parameter. Using the patient condition metric, one or more of an instant state of IBD, a trend of the state of IBD, a change in the medical condition a need for intervention, or a classification of the patient with respect to a risk of exacerbation of IBD can be determined. In various embodiments, external information, such as information from the medical record of the patient, is received, and the medical condition including the state of IBD by analyzing the generated patient condition parameters with the received external information.

At 434, delivery of one or more therapies treating IBD is controlled based on the determined medical condition. At 435, the one or more therapies (e.g., drug and/or neuromodulation therapies) are delivered to the patient.

Figure 5:
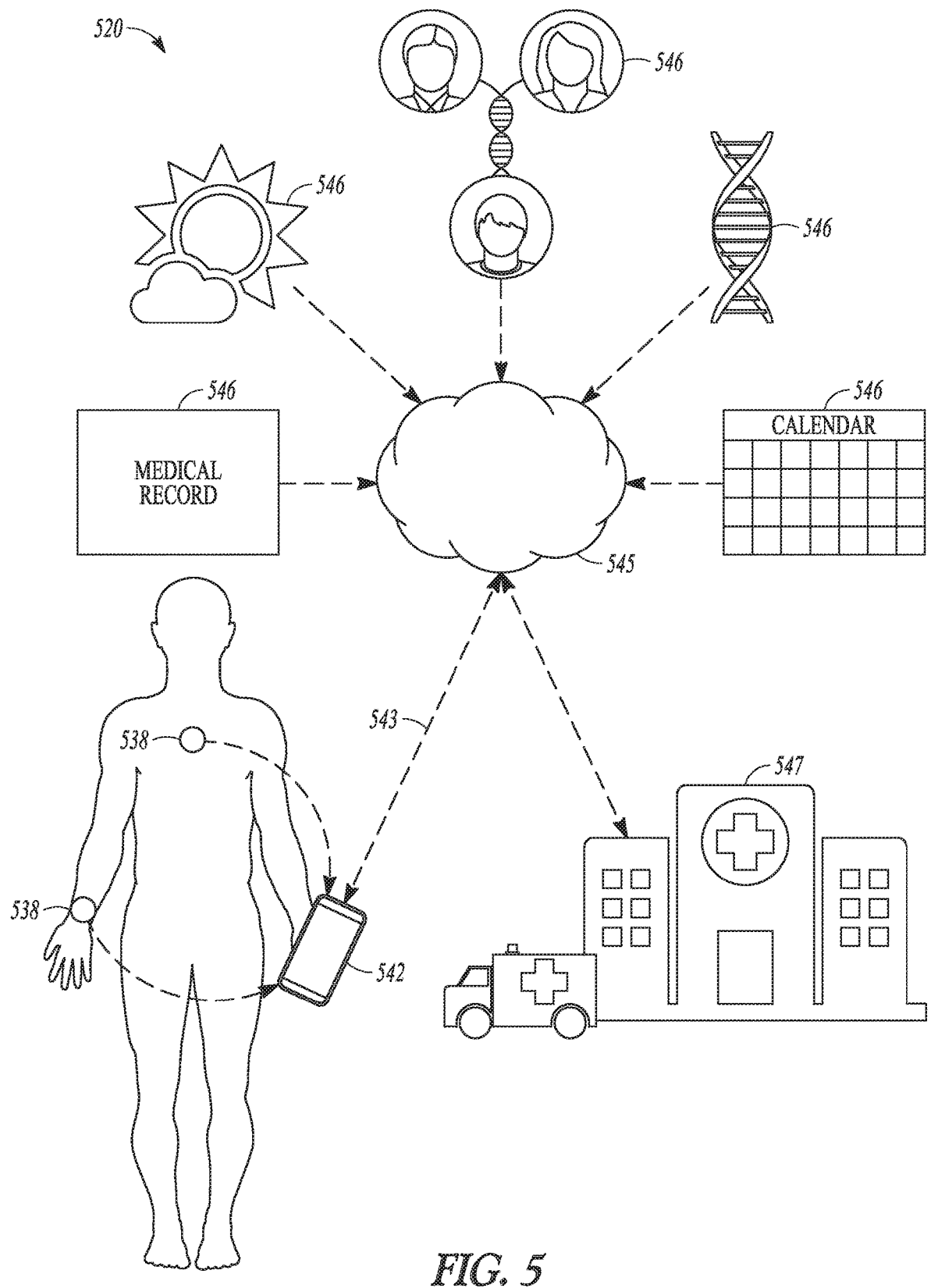
FIG. 5 illustrates an embodiment of a system for monitoring inflammatory bowel disease (IBD).

FIG. 5 illustrates an embodiment of a system 520 for monitoring IBD. System 520 can represent an example of system 320 and can include multiple sensors to monitor several symptoms or physiological markers parameters in the patient to detect earlier signs of an exacerbation of IBD for notifying the patient or the user.

As illustrated in FIG. 5, system 520 can include sensors 538, a portable device 542, a network 545 communicatively coupled to portable device 542 via a wired or wireless communication link 543, sources of external information 546, and a medical facility 547 communicatively coupled to network 545. Medical condition monitoring circuit 300 can be distributed in portable device 542 and/or network 545. In various embodiments, portable device 542 can be implemented as a dedicated device or in a generic device such as a smartphone, a laptop computer, or a tablet computer. Sensors 538 can include sensors 321 each being an implantable or non-implantable sensor communicatively coupled to portable device 542 via a wired or wireless link. In formation such as the patient condition signals, the patient condition parameters, and/or the one or more medical condition indicators can be received and/or produced by portable device 542 and transmitted to network 338 via communication link 336 to be stored, further analyzed, and/or inform the user. External information sources 546 can include any sources of information such as the patient's medical record, weather, time, medical test results, and/or any other data related to the patient's medical condition including the state of IBD. Such information can be transmitted to portable device 542 via communication link 543 when needed (e.g., for the analysis to determine the patient's medical condition including the state of IBD). When the patient's medical condition (e.g., as determined in portable device 542 or network 545) indicates that the patient needs medical attention, a notification will be transmitted to medical facility 547 from network 545.

Figure 6:
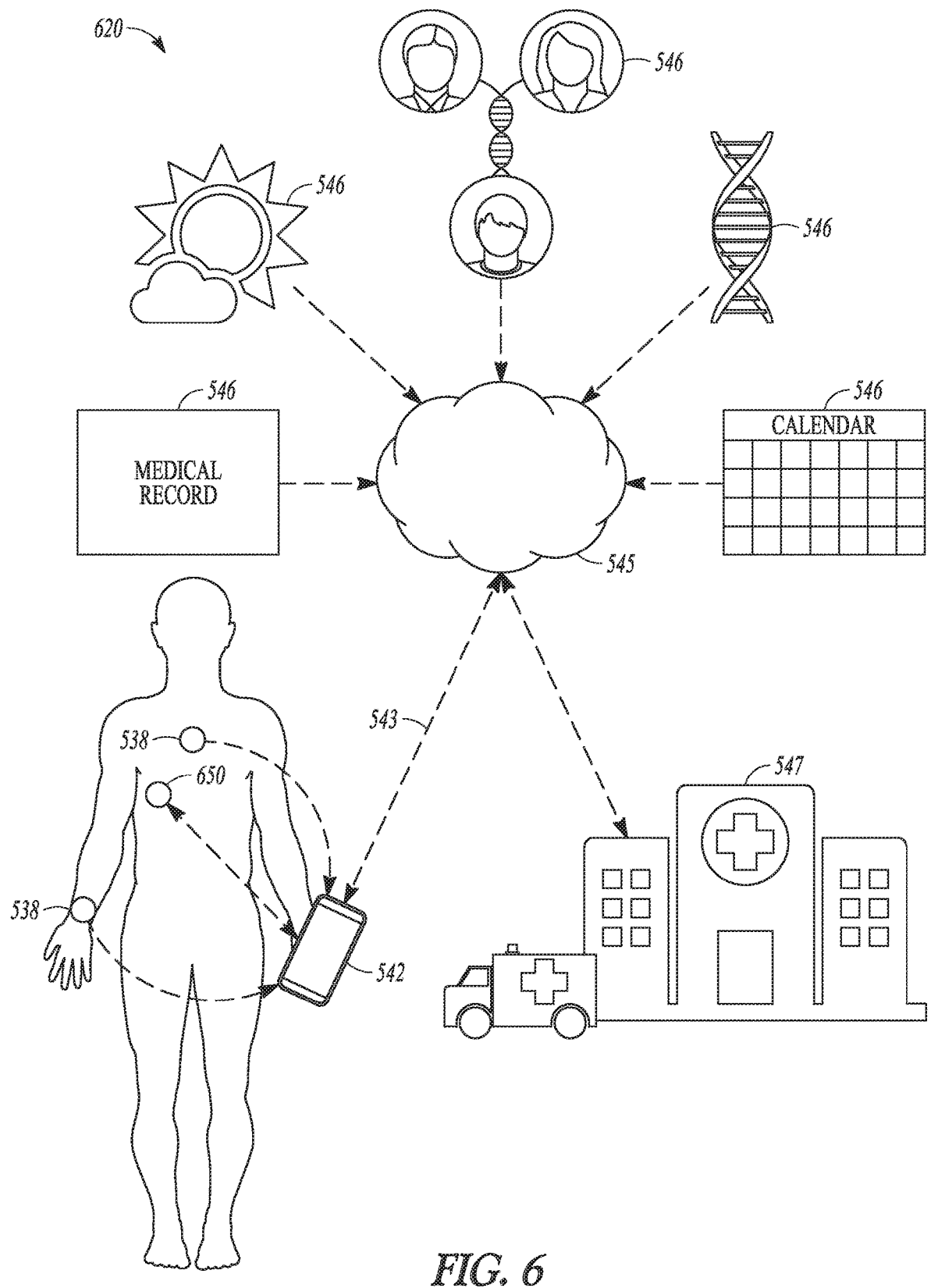
FIG. 6 illustrates an embodiment of a system for closed-loop therapy delivery for treating IBD.

FIG. 6 illustrates an embodiment of a system 620 for closed-loop therapy delivery for treating IBD. System 620 can represent an example of system 320. As illustrated in FIG. 6, system 620 includes the components of system 520 and a therapy device 650. Therapy device 650 can be an example of therapy device 323 and can be an implantable or non-implantable device communicatively coupled to portable device via a wired or wireless communication link. Control circuit 322 can be implemented in portable device 542 and/or therapy device 323. In various embodiments, system 320 is implemented in system 620 as a closed-loop system for monitoring and treating at least IBD.

Figure 7:
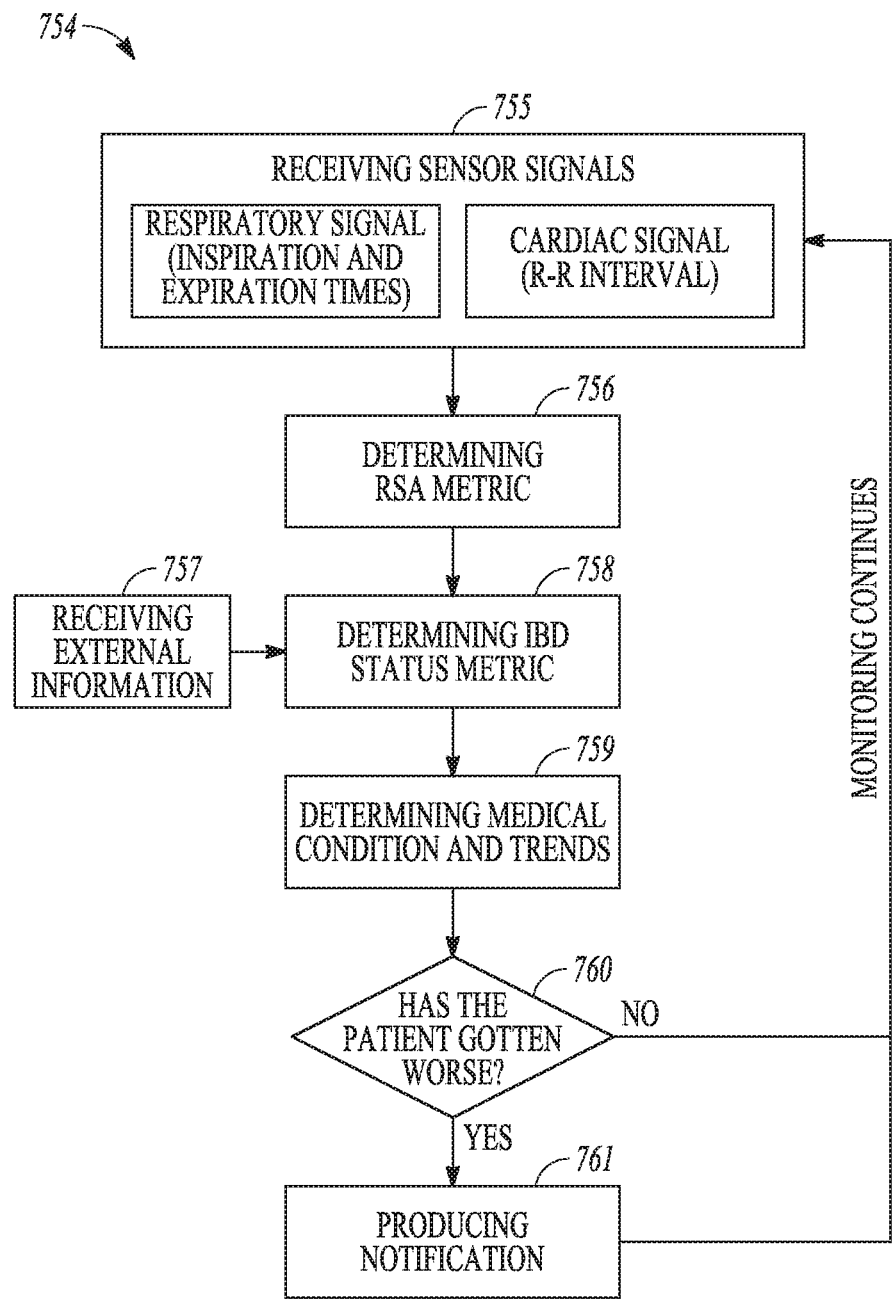
FIG. 7 illustrates an embodiment of a method for monitoring IBD using a respiratory sinus arrhythmia (RSA) measure derived from respiratory and cardiac signals.

FIG. 7 illustrates an embodiment of a method 754 for monitoring IBD using an RSA metric derived from respiratory and cardiac signals. Method 754 can be performed using system 520 or 620.

At 756, sensor signals are received. The sensor signals include a respiratory signal indicative of inspiration and expiration times and a cardiac signal indicative of R-R interval (i.e., as referred to as cardiac cycle length or ventricular rate interval, measure as the time interval between consecutive R-waves). At 756, an RSA metric is determined using the respiratory and cardiac signals. At 757, external information is received. The external information can include any information related to the IBD monitoring that is not directly sensed using sensors coupled to the patient, such as information entered by the patient and/or the user and/or information from the patient's medical record. At 758, an IBD status metric is determined using the RSA metric and the external information. At 759, a medical condition including the state of IBD is determined. In some embodiments, the medical condition can also include state of another inflammatory or other disorder of the patient. If the patient's medical condition including the state of IBD has gotten worse at 760, a notification is produced at 761. The notification can include an alert or alarm for the patient and/or the user to take action such as adjusting a therapy for the IBD. In various embodiments, method 754 can be performed continuously, periodically, in response to triggering signals, or periodically upon being triggered.

Figure 8:
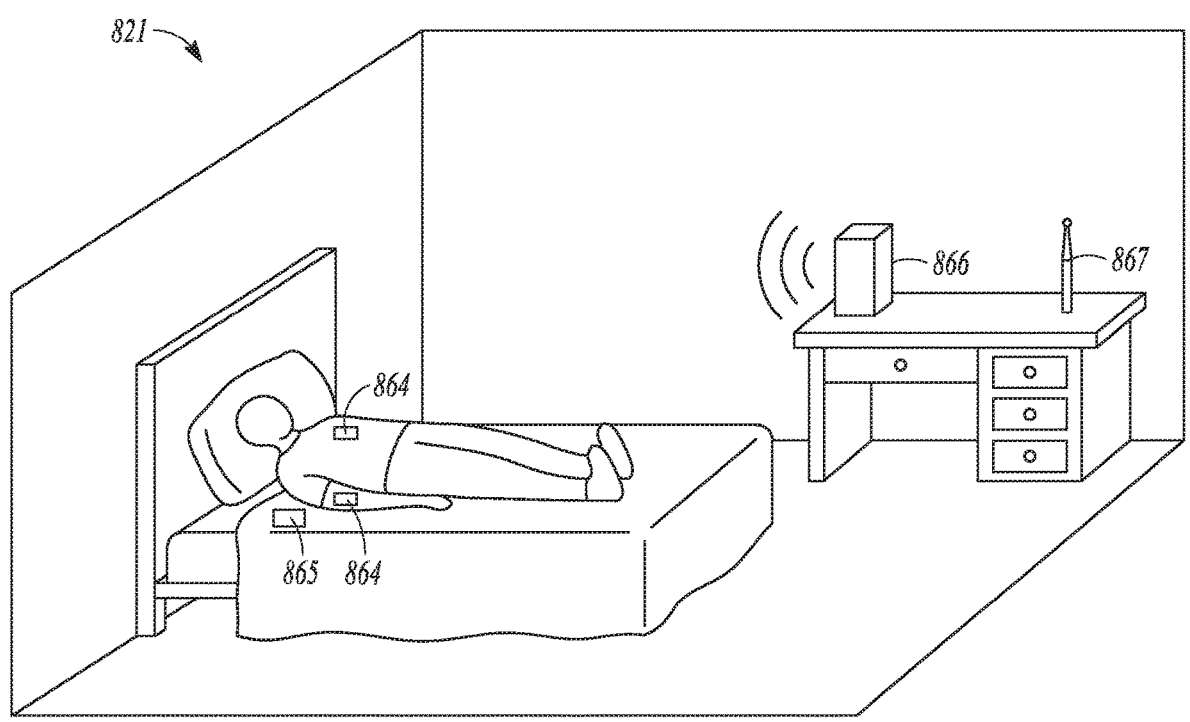
FIG. 8 illustrates an embodiment of a system of non-invasive sensors for monitoring IBD.

FIG. 8 illustrates an embodiment of a system of non-invasive sensors 821 for monitoring IBD. Sensors 821 can be an example of sensors 321 and an example of using non-invasive (non-implantable) sensors for sensors 538 in system 520 or 620. For the purpose of illustration, but not restriction, FIG. 8 shows non-invasive sensors 864, 865, 866, and 867. Sensors 864 can be wearable devices including sensors for sensing, for example, blood volume pulse, temperature, bodily sounds, chemical markers, and/or activity level. Sensor 865 can be a passive bed monitor including one or more sensors for sensing, for example, sleep quality, hate rate, respiratory rate, and/or HRV. Sensor 866 can be a passive in-home monitor including one or more radiowave sensors and/or cameras for sensing, for example, sleep quality, hate rate, and/or respiratory rate. Sensor 867 can be a bodily fluid sensor such as a saliva sensor for inflammatory markers (e.g., incorporated into a toothbrush for daily use).

Figure 9:
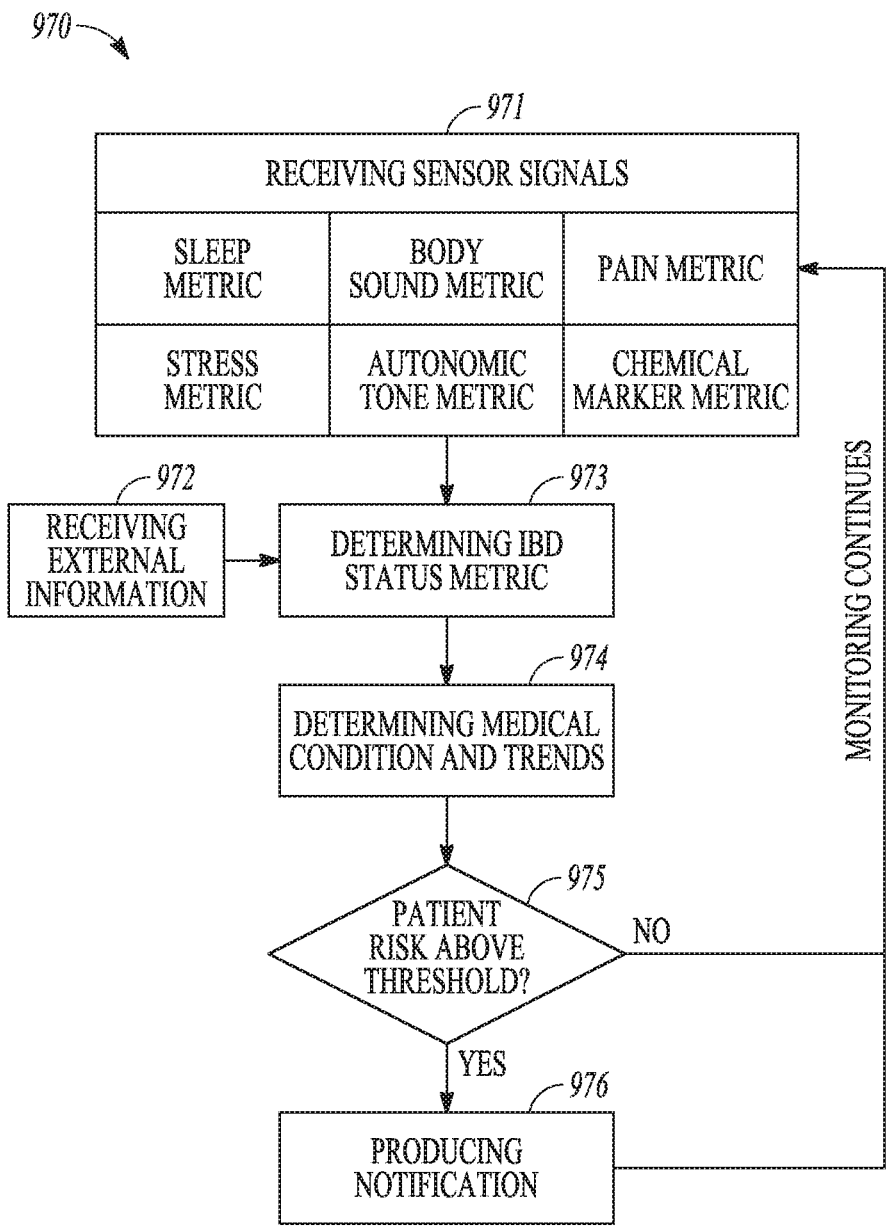
FIG. 9 illustrates an embodiment of a method for monitoring IBD using non-invasive sensors.

FIG. 9 illustrates an embodiment of a method 970 for monitoring IBD using non-invasive sensors. Method 970 can be performed using system 520 or 620 with sensors 538 including non-invasive sensors such as sensors 864, 865, 866, and/or 867.

At 971, sensor signals are received from the non-invasive sensors. The sensor signals allow for generation of patient condition parameters including a sleep metric, a bodily sound metric, a pain metric, a stress metric, an automatic tone metric, and/or a chemical marker metric. The autonomic tone metric can be autonomic tone parameters including heart rate, HRV, blood pressure, blood pressure variability, respiratory rate, RSA, baroreceptor sensitivity, or any other measure of autonomic tone. Examples of such autonomic tone parameters are listed in Table 2, and the autonomic metric can be generated using any one or any combination of these autonomic tone parameters. At 972, external information is received. The external information can include any information related to the IBD monitoring that is not directly sensed using sensors coupled to the patient, such as information entered by the patient and/or the user and/or information from the patient's medical record. At 973, an IBD status metric is determined using the sensor signals and the external information. At 974, a medical condition including the state of IBD is determined. Trends of the medical condition including the state of IBD can also be determined. In some embodiments, the medical condition can also include state of another inflammatory or other disorder of the patient. If the patient's level of risk (e.g., risk of exacerbation of IBD) exceeds a threshold at 975, a notification is produced at 976. The notification can include an alert or alarm for the patient and/or the user to take action such as adjusting a therapy for the IBD. In various embodiments, method 970 can be performed continuously, periodically, in response to triggering signals, or periodically upon being triggered.

Figure 10:
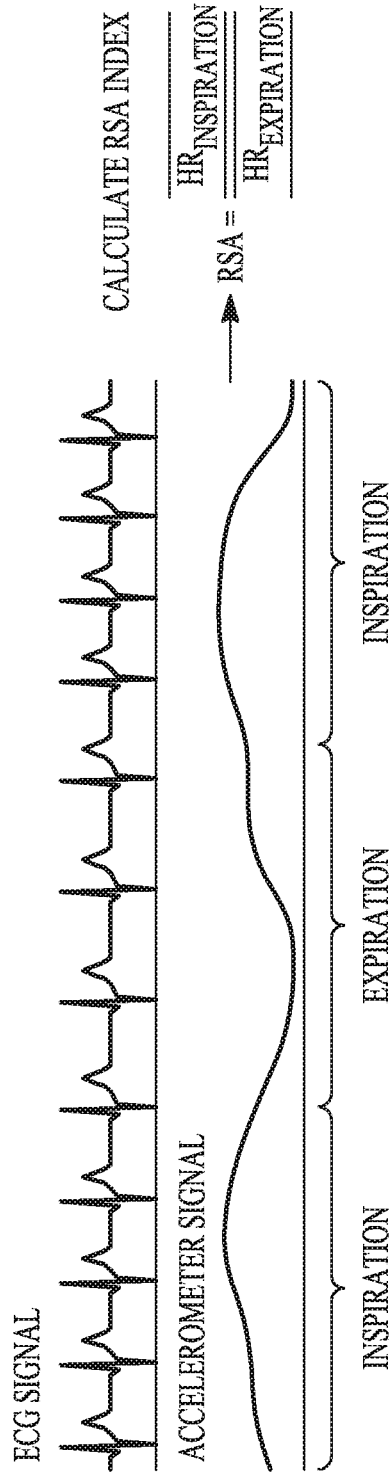
FIG. 10 illustrates an embodiment of a method for monitoring RSA using ECG and accelerometer signals sensed by a wearable patch sensor.
Figure 11:
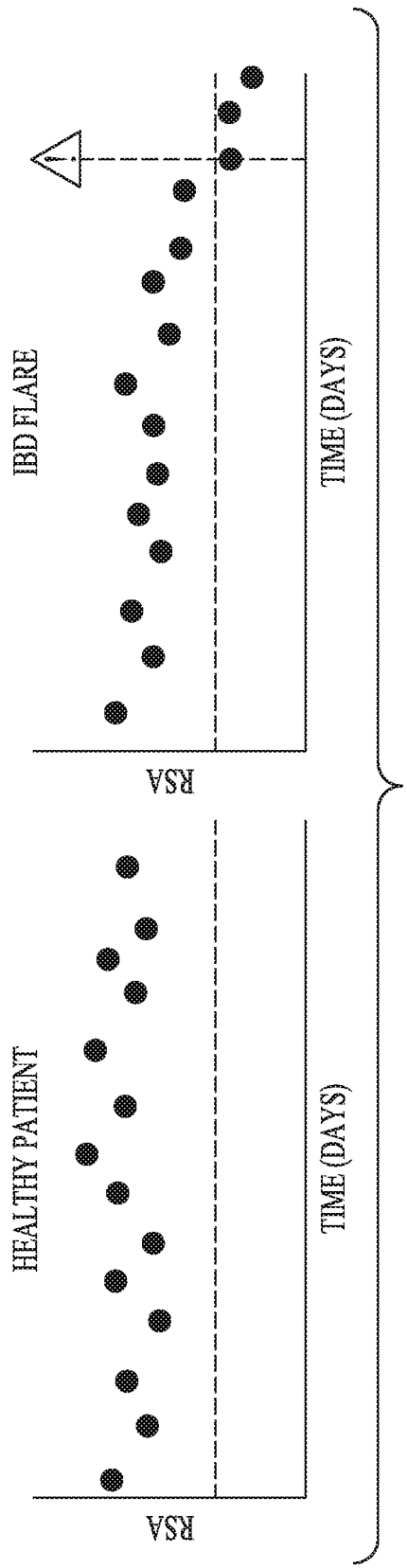
FIG. 11 illustrates an example of RSA information acquired using the method of FIG. 10 and allowing for predicting or detecting IBD exacerbation.

FIG. 10 illustrates an embodiment of a method for monitoring RSA using ECG and accelerometer signals sensed by a wearable patch sensor. Mean heart rates are calculated using R-waves detected from the ECG separately for inspiration and expiration periods detected from the accelerometer signal. An RSA index (representing an autonomic measure) is calculated as a ratio of the mean heart rate during inspiration to the mean heart rate during expiration. FIG. 11 illustrates an example of RSA index plotted against time for a healthy patient and for an IBD patient. IBD exacerbation is detected or predicted when the RSA index falls below a threshold.

Figure 12:
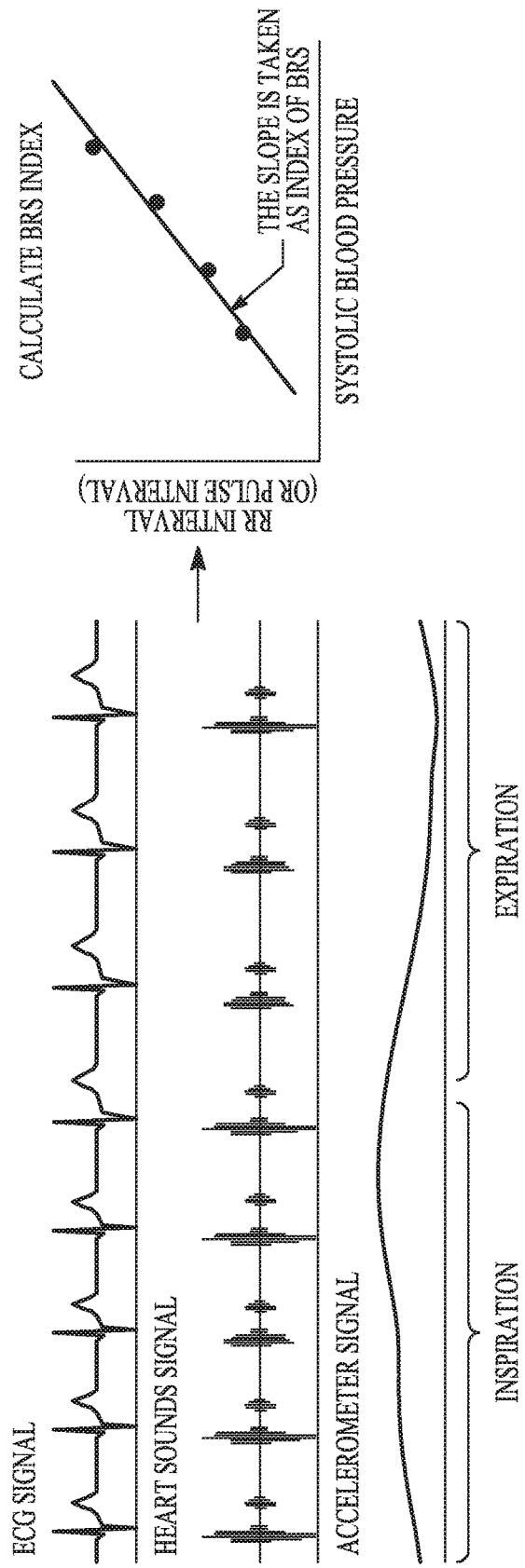
FIG. 12 illustrates an embodiment of a method for monitoring baroreceptor sensitivity (BRS) using ECG, heart sound, and accelerometer signals sensed by an implantable cardiac monitor (ICM).
Figure 13:
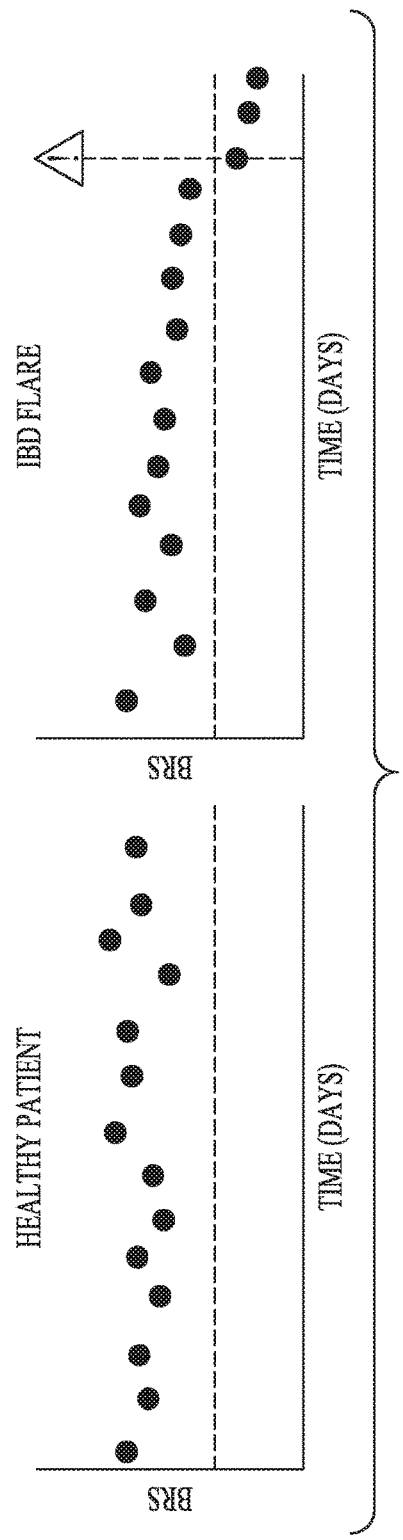
FIG. 13 illustrates an example of BRS information acquired using the method of FIG. 12 and allowing for predicting or detecting IBD exacerbation.

FIG. 12 illustrates an embodiment of a method for monitoring baroreceptor sensitivity (BRS) using ECG, heart sound, and accelerometer signals sensed by an implantable cardiac monitor (ICM). A BRS index (representing an autonomic measure) is calculated as a slope of a curve being the R-R interval against the systolic blood pressure (as indicated by the heart sounds). This represents one of various techniques to quantify spontaneous BRS, and allows for "up" and "down" sequences, which are controlled by different mechanisms, to be evaluated separately. Other techniques include spectral methods that look at the power of the blood pressure and heart rate signals in certain frequency ranges as well as their ratios. FIG. 13 illustrates an example of BRS index plotted against time for a healthy patient and for an IBD patient. IBD exacerbation is detected or predicted when the BRS index falls below a threshold.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

TABLE 1

Sensor Types.

|  | Implantable | No-Contact | Wearable | Mobile Device | Adhesive Patch | Others |
|---|---|---|---|---|---|---|
| ECG sensor | X | X | X | X | X | X |
| accelerometer | X |  | X | X | X | X |
| gyroscope | X |  | X | X | X | X |
| electrical bioimpedance sensor | X |  | X | X | X | X |
| impedance cardiograph sensor | X |  | X |  | X | X |
| optical sensor | X | X | X | X | X | X |
| radiowave sensor |  | X | X |  |  | X |
| microwave sensor |  | X | X |  |  | X |
| pressure sensor | X |  | X |  |  | X |
| PPG sensor | X |  | X |  | X | X |
| microphone | X | X | X | X | X | X |
| GPS/location services sensor | X |  | X | X | X | X |
| chemosensor | X | X | X | X | X | X |
| pH sensor | X |  | X |  | X | X |
| sleep sensor | X | X | X | X | X | X |
| Skin conductance sensor |  |  | X | X | X | X |
| Temperature sensor | X | X | X | X | X | X |

TABLE 2

Examples of autonomic tone parameters.

| Biomarker | Physiology/Definition | Sympathetic Activity Correlate |
|---|---|---|
| Autonomic Measures | | |
| Heart Rate (HR) | Indicator of sympathetic tone. Higher HR indicates higher sympathetic nervous activity (SNA) | (+) correlation |
| Heart Rate Variability (HRV) | Measure of autonomic balance. Autonomic dysfunction at the base of many disease states. Appears to be a reliable marker for adaptive stress, including both dynamic and cumulative load. Sympathetic activation decreases HRV | (−) correlation |
| AVNN | Average of all NN intervals | (−) correlation |
| SDNN | Standard deviation of all NN intervals (Measure of long term HRV) | (−) correlation |
| SDANN | Standard deviation of the averages of NN intervals in all 5-minute segments of a 24-hour recording (Measure of long term HRV) | (−) correlation |
| SDNNIDX | Mean of the standard deviations of NN intervals in all 5-minute segments of a 24-hour recording | (−) correlation |
| RMSSD | Square root of the mean of the squares of differences between adjacent NN intervals. (Measure of short term HRV) | (−) correlation |
| pNN50 | Percentage of differences between adjacent NN intervals that are greater than 50 ms. | (−) correlation |
| vLF | Total spectral power of all NN intervals between 0.003 and 0.04 Hz | (−) correlation |
| LF | Total spectral power of all NN intervals between 0.04 and 0.15 Hz | (−) correlation |
| HF | Total spectral power of all NN intervals between 0.15 and 0.4 Hz | (−) correlation |
| LF/HF | Ratio of low to high frequency power | (+) correlation |

TABLE 2-continued

Examples of autonomic tone parameters.

| Biomarker | Physiology/Definition | Sympathetic Activity Correlate |
|---|---|---|
| total power | total spectral power of al NN intervals up to 0.4 Hz | |
| UsEn | Ultra-short entropy (UsEn) is a nonlinear approach that is thought to offer an insight into the overall structure of the HR regulatory system with a connection between disorder and a decrease in entropy | (−) correlation |
| alpha 1 | short term fractal scaling exponent measures the qualitative characteristics and correlation features of HR behavior. | (+) correlation |
| Galvanic Skin Response (GSR) | SNA causes sweat glands to fill up and skin conductance increases creating skin conductance fluctuations. | (+) correlation |
| Photo-Plethysmographic (PPG) | Reduction in the amplitude of PPG is caused by peripheral vasoconstriction and the nociception response during general anesthesia. Vasoconstriction as a result of increased SNA. | (−) correlation |
| Pulse Rate Variability (PRV) | Could be a replacement measure for HRV. Can be used to estimate HRV at rest, but in motion can become less reliable/accurate | (−) correlation |
| Blood Pressure (BP) | Marker of sympathetic tone. Increased sympathetic causes vasoconstriction and thus elevated BP. | (+) correlation |
| Pulse Transit Time & Pulse Wave Amplitude (Alternative measure for BP) | Vasoconstriction is a result of sympathetic activation which directly impacts the pulse transit time and pulse wave amplitude. | (−) correlation |
| Respiration Rate (RR) | Measure of sympathetic tone. Elevated respiratory rate corresponds to increased sympathetic activation | (+) correlation |
| Pupil Diameter | Dilation of the pupil is indicative of sympathetic activation | (+) correlation |
| Respiratory Sinus Arrhythmia (RSA) | RSA is a measure to assess cardiac autonomic function. RSA decreases in the presence of increased sympathetic activity/decreased parasympathetic activity. | (−) correlation |
| Baroreceptor Sensitivity | Decreased baroreceptor response is associated over active sympathetic nervous system in disease states. | (−) correlation |
| Normalized Pulse Volume (NPV) | Sympathetic tone causes vascular constriction. This vascular tone can be measured in several locations on the body to indicate sympathetic tone. NPV can be derived from the finger tip using PPG. It can also be derived from the bottom of the ear canal. | (−) correlation |
| Chemical Markers | | |
| Norepinephrine | Activation of the sympathetic nervous system results in an increase in the neurotransmitter norepinephrine | (+) correlation |
| Acetylcholine | Activation of the parasympathetic nervous system results in an increase in the neurotransmitter acetylcholine | (−) correlation |

What is claimed is:

1. A system for monitoring and treating a medical condition of a patient, comprising:
   signal inputs configured to receive patient condition signals indicative of a state of inflammatory bowel disease (IBD);
   a trigger input configured to receive one or more triggering signals including at least one of an activity signal indicative of the patient's activity level or a sleep signal indicative of whether the patient is sleeping;
   a signal processing circuit configured to process the received patient condition signals, to adjust the processing of the received patient condition signals using the received one or more triggering signals, and to generate patient condition parameters using the processed patient condition signals, the patient condition parameters indicative of the state of IBD and including an autonomic measure generated for a constant or known physical state of the patient indicated by the at least one of the activity signal or the sleep signal, the autonomic measure including a baroreceptor sensitivity; and
   a medical condition analyzer configured to determine the medical condition of the patient using the generated patient condition parameters, the medical condition analyzer including:
     a physiological marker input configured to receive one or more physiological marker parameters of the patient condition parameters, the one or more physiological marker parameters including the autonomic measure and each representative of a physiological marker of IBD;
     a quality of life input to receive one or more quality of life parameters of the patient condition parameters, the one or more quality of life parameters each being a measure of quality of life of the patient; and
     a parameter analysis circuit configured to analyze the generated patient condition parameters and determine the medical condition including the state of IBD using an outcome of the analysis, the analysis including comparing the autonomic measure to a threshold.

2. The system of claim 1, further comprising:
   a therapy device configured to deliver one or more therapies treating IBD; and a control circuit configured to control the delivery of the one or more therapies based on the determined medical condition.

3. The system of claim 1, wherein the parameter analysis circuit is configured to produce a patient condition metric being a linear or nonlinear combination of at least two parameters of the generated patient condition parameters and to determine the medical condition based on the patient condition metric.

4. The system of claim 3, wherein the medical condition analyzer comprises a notification circuit configured to produce one or more medical condition indicators based on the determined medical condition and output the produced one or more medical condition indicators, the one or more medical condition indicators indicating at least an instant state of IBD.

5. The system of claim 4, further comprising a storage device configured to store the determined medical condition, and wherein the analysis circuit is further configured to produce and analyze a trend of the state of IBD, and the notification circuit is configured to detect changes in the medical condition from the trend of the state of IBD and to produce the one or more medical condition indicators to further indicate one or more of the trend of the state of IBD or the detected changes in the medical condition.

6. The system of claim 4, wherein the notification circuit is configured to detect a need for intervention from the determined medical condition and to generate an alert or notification of the one or more medical condition indicators in response to a detection of the need for intervention.

7. The system of claim 4, wherein the notification circuit is configured to classify the patient with respect to a risk of exacerbation of IBD based on the one or more medical condition indicators and to produce the one or more medical condition indicators to further indicate the classification.

8. The system of claim 1, wherein the medical condition analyzer further comprises a chemical marker input configured to receive one or more chemical marker parameters of the patient condition parameters, the one or more chemical marker parameters each representative of a chemical marker of IBD.

9. The system of claim 1, wherein the medical condition analyzer further comprises an environmental information input configured to receive one or more environmental parameters of the patient condition parameters, the one or more environmental parameters indicative of an environment of the patient.

10. The system of claim 1, wherein the medical condition analyzer further comprises an external information input configured to receive external information including at least information from the medical record of the patient, and wherein the parameter analysis circuit configured to analyze the generated patient condition parameters with the received external information.

11. The system of claim 1, comprising one or more sensors configured to sense one or more signals related to the medical conditions and to produce one or more sensor signals of the patient condition signals and an implantable medical device including at least the signal inputs, the signal processing circuit, and the medical condition analyzer, the one or more sensors including at least one implantable sensor.

12. The system of claim 1, wherein the signal processing circuit is configured to adjust the processing of the received patient condition signals using the received one or more triggering signals by adjusting a sampling rate using the received one or more triggering signals.

13. A method for monitoring and treating a medical condition of a patient, comprising:
receiving patient condition signals indicative of a medical condition including a state of inflammatory bowel disease (IBD);
processing the received patient condition signals and generating patient condition parameters indicative of the medical condition including the state of IBD using the processed patient condition signals using a signal processing circuit, including generating at least one or more physiological marker parameters and one or more quality of life parameters, the one or more physiological marker parameters including an autonomic measure and each representative of a physiological marker of IBD, the one or more quality of life parameters each being a measure of quality of life of the patient;
receiving one or more triggering signals including at least one of an activity signal indicative of the patient's activity level or a sleep signal indicative of whether the patient is sleeping;
adjusting the generation of the patient condition parameters using the received one or more triggering signals, including generating the autonomic measure for a constant or known physical state of the patient indicated by the at least one of the activity signal or the sleep signal, the generation of the autonomic measure including generating a baroreceptor sensitivity; and
determining the medical condition including the state of IBD by analyzing the generated patient condition parameters using a parameter analysis circuit of a medical condition analyzer, the analysis including comparing the autonomic measure to a threshold.

14. The method of claim 13, further comprising:
delivering one or more therapies treating IBD; and
controlling the delivery of the one or more therapies based on the determined medical condition.

15. The method of claim 13, wherein determining the medical condition comprises:
producing a patient condition metric being a linear or nonlinear combination of at least two parameters of the generated patient condition parameters; and
determining, using the patient condition metric, one or more of: an instant state of IBD, a trend of the state of IBD, a change in the medical condition, a need for intervention, or a classification of the patient with respect to a risk of exacerbation of IBD.

16. The method of claim 13, wherein generating the patient condition parameters further comprises generating one or more chemical marker parameters each representative of a chemical marker of IBD.

17. The method of claim 13, wherein generating the patient condition parameters further comprises generating one or more environmental parameters indicative of an environment of the patient.

18. The method of claim 13, further comprising receiving external information including at least information from the medical record of the patient, and wherein determining the medical condition including the state of IBD comprises analyzing the generated patient condition parameters with the received external information.

19. The method of claim 13, furthering comprising sensing one or more signals related to the medical conditions and producing one or more sensor signals of the patient condition signals using one or more sensors.

20. The method of claim 13, wherein generating the autonomic measure further comprises generating a respiratory sinus arrhythmia (RSA) index being a ratio of a mean heart rate during inspiration to a mean heart rate during expiration.

\* \* \* \* \*